United States Patent [19]

Backus et al.

[11] Patent Number: 5,582,988

[45] Date of Patent: Dec. 10, 1996

[54] METHODS FOR CAPTURE AND SELECTIVE RELEASE OF NUCLEIC ACIDS USING WEAKLY BASIC POLYMER AND AMPLIFICATION OF SAME

[75] Inventors: John W. Backus, Williamson; Tobias E. Ekeze, Rochester; Jerome C. Swartz, Rochester; Richard C. Sutton, Rochester; Ignazio S. Ponticello, Pittsford; JoAnne H. Kerschner, Rochester; John B. Findlay, Webster, all of N.Y.

[73] Assignee: Johnson & Johnson Clinical Diagnostics, Inc., Rochester, N.Y.

[21] Appl. No.: 306,870

[22] Filed: Sep. 15, 1994

[51] Int. Cl.$^6$ ............................ C12Q 1/68; C12Q 1/70
[52] U.S. Cl. ............................................... 435/6; 435/5
[58] Field of Search ............................ 435/6, 5; 536/23.1

[56] References Cited

U.S. PATENT DOCUMENTS

| | | | |
|---|---|---|---|
| 4,055,469 | 10/1977 | Snoke et al. | 195/66 |
| 4,056,666 | 11/1977 | Seita et al. | 526/29 |
| 4,066,827 | 1/1978 | Seita et al. | 526/50 |
| 4,119,590 | 10/1978 | Seita et al. | 260/8 |
| 4,839,231 | 6/1989 | Vandekerckhove | 428/441 |
| 4,994,192 | 2/1991 | Corin et al. | 210/782 |
| 5,053,326 | 10/1991 | Renz | 435/6 |

FOREIGN PATENT DOCUMENTS

| | | | |
|---|---|---|---|
| 574227 | 12/1993 | European Pat. Off. | C12Q 1/68 |
| 63/003798 | 6/1986 | Japan | C07K 3/24 |

*Primary Examiner*—Stephanie W. Zitomer
*Assistant Examiner*—Eggerton Campbell

[57] ABSTRACT

Nucleic acids can be made available for amplification or other treatment after lysis by contacting the lysate with specific weakly basic polymers to form a precipitate with the nucleic acids at acidic pH. After removing non-precipitated materials, the pH is then made basic, thereby releasing the nucleic acids from the polymer. This method for preparing specimen samples is simple and quite rapid, and the released nucleic acids can be further treated in hybridization assays or amplification procedures. The weakly basic polymers are water-soluble and cationic at acidic pH, but neutral in charge at basic pH.

21 Claims, 2 Drawing Sheets

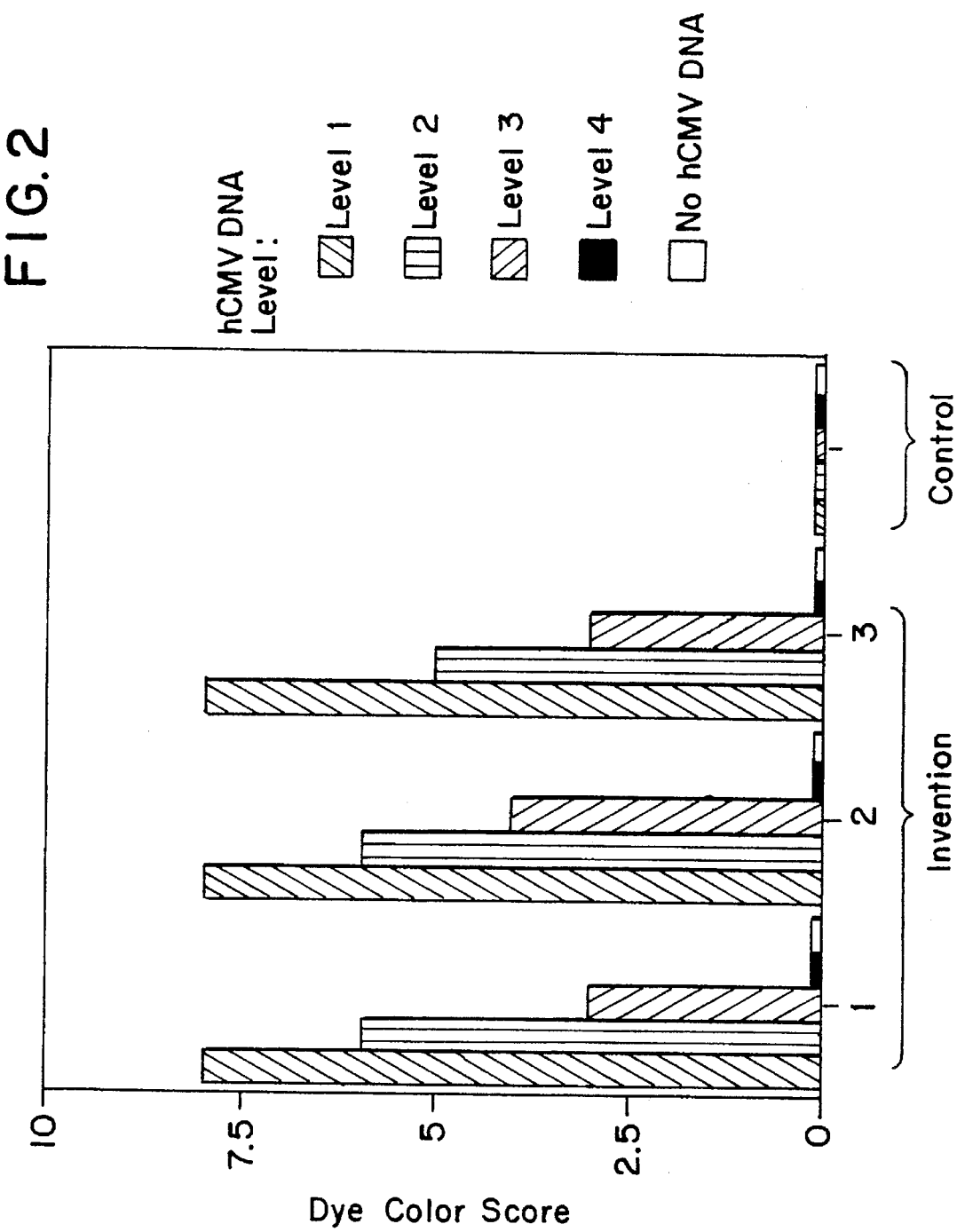

5,582,988

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 27 nucleotides
        ( B ) TYPE: Nucleic acid
        ( C ) STRANDEDNESS: Single
        ( D ) TOPOLOGY: Linear ( i i ) MOLECULE TYPE: Primer for hCMV DNA ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: Unknown ( x i ) SEQUENCE DESCRIPTION: SEQ ID NO:1:

CATTCCCACT GACTTTCTGA CGCACGT        27

( 2 ) INFORMATION FOR SEQ ID NO:2:

( i ) SEQUENCE CHARACTERISTICS:
        ( A ) LENGTH: 24 nucleotides
        ( B ) TYPE: Nucleic acid
        ( C ) STRANDEDNESS: Single
        ( D ) TOPOLOGY: Linear ( i i ) MOLECULE TYPE: Primer for hCMV DNA ( i i i ) HYPOTHETICAL: No ( i v ) ANTI-SENSE: No ( v i ) ORIGINAL SOURCE: Synthetically prepared ( v i i ) IMMEDIATE SOURCE: Synthetically prepared ( x ) PUBLICATION INFORMATION: None ( x i ) SEQUENCE DESCRIPTION: SEQ ID NO:2:

TGAGGTCGTG GAACTTGATG GCGT        24

( 2 ) INFORMATION FOR SEQ ID NO:3:

( i ) SEQUENCE CHARACTERISTICS:
        ( A ) LENGTH: 30 nucleotides
        ( B ) TYPE: Nucleic acid
        ( C ) STRANDEDNESS: Single
        ( D ) TOPOLOGY: Linear ( i i ) MOLECULE TYPE: Capture probe for hCMV DNA (i i i) HYPOTHETICAL: No (i v) ANTI-SENSE: No (v i) ORIGINAL SOURCE: Synthetically prepared (v i i) IMMEDIATE SOURCE: Synthetically prepared (x) PUBLICATION INFORMATION: None (x i) SEQUENCE DESCRIPTION: SEQ ID NO:3:

GGTCATCGCC GTAGTAGATG CGTAAGGCCT                    30

(2) INFORMATION FOR SEQ ID NO:4:

(i) SEQUENCE CHARACTERISTICS:
 (A) LENGTH: 25 nucleotides
 (B) TYPE: Nucleic acid
 (C) STRANDEDNESS: Single
 (D) TOPOLOGY: Linear (i i) MOLECULE TYPE: Primer for Mycobacterium
 tuberculosis DNA (i i i) HYPOTHETICAL: No (i v) ANTI-SENSE: No (v i) ORIGINAL SOURCE: Synthetically prepared (v i i) IMMEDIATE SOURCE: Synthetically prepared (x) PUBLICATION INFORMATION: Unknown (x i) SEQUENCE DESCRIPTION: SEQ ID NO:4:

GAGATCGAGC TGGAGGATCC GTACG                         25

(2) INFORMATION FOR SEQ ID NO:5:

(i) SEQUENCE CHARACTERISTICS:
 (A) LENGTH: 25 nucleotides
 (B) TYPE: Nucleic acid
 (C) STRANDEDNESS: Single
 (D) TOPOLOGY: Linear (i i) MOLECULE TYPE: Primer for Mycobacterium
 tuberculosis DNA (i i i) HYPOTHETICAL: No (i v) ANTI-SENSE: No (v i) ORIGINAL SOURCE: Synthetically prepared (v i i) IMMEDIATE SOURCE: Synthetically prepared (x) PUBLICATION INFORMATION: None (x i) SEQUENCE DESCRIPTION: SEQ ID NO:5:

AGCTGCAGCC CAAAGGTGTT GGACT                         25

(2) INFORMATION FOR SEQ ID NO:6:

(i) SEQUENCE CHARACTERISTICS:
 (A) LENGTH: 30 nucleotides
 (B) TYPE: Nucleic acid
 (C) STRANDEDNESS: Single
 (D) TOPOLOGY: Linear (i i) MOLECULE TYPE: Capture probe for
 Mycobacterium tuberculosis DNA (i i i) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:6:

CGAAATCGCT GCGGTGGCCG CAATCTGCTC                    30

(2) INFORMATION FOR SEQ ID NO:7:

(i) SEQUENCE CHARACTERISTICS:
    (A) LENGTH: 28 nucleotides
    (B) TYPE: Nucleic acid
    (C) STRANDEDNESS: Single
    (D) TOPOLOGY: Linear (ii) MOLECULE TYPE: HIV1 proviral DNA primer (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: Unknown (xi) SEQUENCE DESCRIPTION: SEQ ID NO:7:

TTTGGTCCTT GTCTTATGTC CAGAATGC                      28

(2) INFORMATION FOR SEQ ID NO:8:

(i) SEQUENCE CHARACTERISTICS:
    (A) LENGTH: 28 nucleotides
    (B) TYPE: Nucleic acid
    (C) STRANDEDNESS: Single
    (D) TOPOLOGY: Linear (ii) MOLECULE TYPE: HIV1 proviral DNA primer (iii) HYPOTHETICAL: No (iv) ANTI-SENSE: No (vi) ORIGINAL SOURCE: Synthetically prepared (vii) IMMEDIATE SOURCE: Synthetically prepared (x) PUBLICATION INFORMATION: None (xi) SEQUENCE DESCRIPTION: SEQ ID NO:8:

ATAATCCACC TATCCCAGTA GGAGAAAT                      28

(2) INFORMATION FOR SEQ ID NO:9:

(i) SEQUENCE CHARACTERISTICS:
    (A) LENGTH: 41 nucleotides
    (B) TYPE: Nucleic acid
    (C) STRANDEDNESS: Single
    (D) TOPOLOGY: Linear (ii) MOLECULE TYPE: HIV1 proviral DNA probe (iii) HYPOTHETICAL: No (iv) ANTI-SENSE: No (vi) ORIGINAL SOURCE: Synthetically prepared (vii) IMMEDIATE SOURCE: Synthetically prepared ( x ) PUBLICATION INFORMATION: None ( x i ) SEQUENCE DESCRIPTION: SEQ ID NO:9:

ATCCTGGAAT TAAATAAAAT AGTAAGAATG TATAGCCCTA C   4 1

METHODS FOR CAPTURE AND SELECTIVE RELEASE OF NUCLEIC ACIDS USING WEAKLY BASIC POLYMER AND AMPLIFICATION OF SAME

FIELD OF THE INVENTION

This invention relates to a method for preparing a sample by capture and selective release of nucleic acids for detection. In particular, it relates to a method for capture and release of nucleic acids for subsequent treatment such as amplification. It also relates to a test kit for use in the method.

BACKGROUND OF THE INVENTION

Technology to detect minute quantities of nucleic acids has advanced rapidly over the last two decades including the development of highly sophisticated amplification techniques such as polymerase chain reaction (PCR). Researchers have readily recognized the value of such technology to detect nucleic acids which are indicative of diseases and genetic features in human or animal test specimens. The use of probes and primers in such technology is based upon the concept of complementarity, that is, the bonding of two strands of a nucleic acid by hydrogen bonds between complementary nucleotides (also known as nucleotide pairs).

PCR is a significant advance in the art to allow detection of very small concentrations of a targeted nucleic acid. The details of PCR are described, for example, in U.S. Pat. No. 4,683,195 (Mullis et al), U.S. Pat. No. 4,683,202 (Mullis) and U.S. Pat. No. 4,965,188 (Mullis et al), although there is a rapidly expanding volume of literature in this field.

In order to effectively amplify and detect a target nucleic acid, it is usually necessary to isolate that nucleic acid from cellular and other specimen debris. Various lysing procedures are known, including freezing, treatment with digesting enzyme such as proteases (for example, Proteinase K), boiling, and use of various detergents (see for example U.S. Ser. No. 178,202, filed Apr. 6, 1988 by Higuchi, and EP-A-0 428 197, published May 22, 1991), solvent precipitations and heating protocols.

Once nucleic acids are extracted from cells or virus particles, however, there remains a need to separate them from other materials in the lysate in a simple and cost effective manner. One material known to complex with nucleic acids is polyethyleneimine and various chemical derivatives. It has been used to precipitate nucleic acids as contaminants in processes for isolating enzymes, and in affinity columns for capturing nucleic acids.

More recently, our colleagues have used polyethyleneimine in combination with an anionic phosphate ester surfactant to capture and selectively isolate nucleic acids. While this technique has been used with some success, it requires the use of two separate reagents in different steps in carefully controlled amounts. That is, the amount of phosphate ester surfactant used is dependent upon the amount of polyethyleneimine which is present in the precipitate with the nucleic acids. An improvement has been sought to reduce the number of steps and reagents needed for capture and isolation of nucleic acids.

SUMMARY OF THE INVENTION

The problems noted above are overcome with a method for providing a nucleic acid from a lysate comprising the steps of:

A) at a pH of less than 7, contacting a lysate suspected of containing a nucleic acid with a water-soluble, weakly basic polymer in an amount sufficient to form a water-insoluble precipitate of the weakly basic polymer with all nucleic acids present in the lysate, B) separating the water-insoluble precipitate from the lysate, and C) contacting the precipitate with a base to raise the solution pH to greater than 7, and thereby releasing the nucleic acids from the weakly basic polymer, the weakly basic polymer comprising recurring units derived by addition polymerization of one or more ethylenically unsaturated polymerizable monomers having an amine group which can be protonated at acidic pH.

This invention also provides a method for the amplification and detection of a target nucleic acid comprising:

I) providing a target nucleic acid using the steps of:

A) at a pH of less than 7, contacting a lysate suspected of containing a target nucleic acid with a water-soluble, weakly basic polymer in an amount sufficient to form a water-insoluble precipitate of the weakly basic polymer with all nucleic acids present in the lysate, including the target nucleic acid, B) separating the water-insoluble precipitate from the lysate, and C) contacting the precipitate with a base to raise the solution pH to greater than 7, and thereby releasing the nucleic acids, including the target nucleic acid, from the weakly basic polymer, the weakly basic polymer comprising recurring units derived by addition polymerization of one or more ethylenically unsaturated polymerizable monomers having an amine group which can be protonated at acidic pH, II) amplifying the target nucleic acid present among the released nucleic acids, and III) detecting the amplified target nucleic acid.

A test kit for amplification of a target nucleic acid comprises, separately packaged:

a) an amplification reaction mixture comprising one or more amplification reagents, and b) a weakly basic polymer comprising recurring units derived by addition polymerization of one or more ethylenically unsaturated polymerizable monomers having an amine group which can be protonated at acidic pH.

The present invention provides a rapid, simple and effective method for selectively isolating and providing nucleic acids for further treatment, such as hybridization assays or amplification procedures. This invention overcomes the problems noted above relating to conventional isolation means, including the use of polyethyleneimine. In addition, the problems presented by the use of polyethyleneimine combined with a fluorinated phosphate surfactant are also avoided because the surfactant is not needed. The sample preparation method of this invention is not tedious and requires a minimum of steps, thereby making it more readily automated. It usually can be carried out within about 15 minutes (preferably within 10 minutes).

These advantages are provided by using in place of the polyethyleneimine a "weakly basic" polymer which is cationic and water-soluble at acidic pH, but deprotonates at a basic pH which is significantly above the pKa of the polymer. By "weakly basic" is meant that the polymer pKa is less than 7, and more likely less than 6.5. Thus, the polymer can be used at low pH to precipitate nucleic acids because of the ionic interaction of the cationic polymer and the anionic phosphate backbone of nucleic acids.

After removing noncomplexed materials, and upon a pH adjustment to basic conditions, the nucleic acids are released (or decomplexed) from the weakly basic polymer of the precipitate and available for further treatment, such as amplification. The amplification procedures can be carried out under basic conditions.

BRIEF DESCRIPTION OF THE DRAWING

FIG. 2 illustrates data obtained in Example 4 below in bar graphical form.

DETAILED DESCRIPTION OF THE INVENTION

Figure 1:
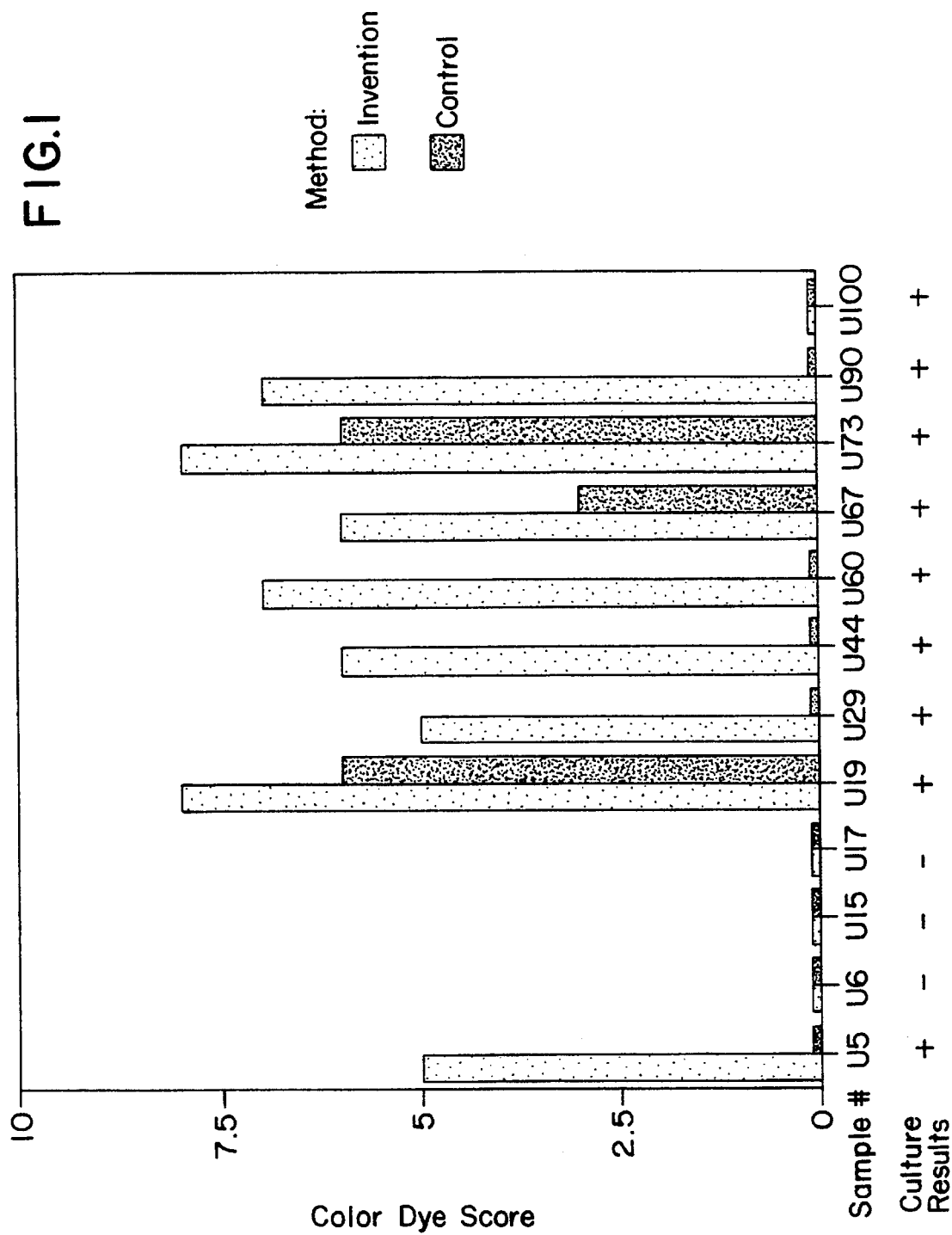
FIG. 1 illustrates data obtained in Example 3 below in bar graphical form.

The present invention is especially suited for the extraction and detection of one or more target nucleic acids present in a sample of any type collected from animals, humans, environmental or microbial specimens. The nucleic acids so obtained can be further treated by subjecting them to conventional hybridization assays, the procedures of which are well known in the art (for example, U.S. Pat. No. 4,994,373, incorporated herein by reference with respect to the hybridization technology).

However, for the sake of brevity, the remaining discussion will be directed to preferred embodiments whereby the nucleic acids are subjected to amplification procedures, particularly PCR. However, the scope of this invention is not intended to be so limited because other amplification techniques (such as LCR) can be used also.

The general principles and conditions for amplification and detection of nucleic acids using polymerase chain reaction are quite well known, the details of which are provided in numerous references including U.S. Pat. No. 4,683,195 (Mullis et al), U.S. Pat. No. 4,683,202 (Mullis), U.S. Pat. No. 4,965,188 (Mullis et al) and WO-A-91/12342. The noted U.S. patents are incorporated herein by reference. In view of the teaching in the art and the specific teaching provided herein, a worker skilled in the art should have no difficulty in practicing the present invention by combining the preparatory method of this invention with polymerase chain reaction procedures, or with any other amplification procedure known in the art.

Other amplification procedures which can be used in the practice of this invention include, but are not limited to, ligase chain reaction as described, for example, in EP-A-0 320 308 (published December, 1987) and EP-A-0 439 182 (published January, 1990).

Test specimens can include cellular or viral material, hair, body fluids or other materials containing genetic DNA or RNA, or DNA or RNA from infectious agents which can be detected. The target nucleic acid can be extracted from any suitable human, animal, microbial, viral or plant source. In addition, target nucleic acids may be isolated from oncogenic cells.

Bacteria which can be detected include, but are not limited to, bacteria which may be found in blood, Salmonella spp., Streptococcus spp., Chlamydia spp., Neisseria spp., Mycobacterium spp (such as *Mycobacterium tuberculosis* and *Mycobacterium avium* complex), Mycoplasma spp. (such as *Mycoplasma Haemophilus* influenzae and *Mycoplasma pneumoniae*), *Legionella pneumophila*, *Borrelia burgdorferei*, *Pneumocystis carinii*, *Clostridium difficile*, Campylobacter spp., Yersinia spp., Shigella spp. and Listeria spp.. Viruses which are detectable include, but are not limited to, herpes simplex viruses, Epstein Barr virus, cytomegalovirus, human papilloma viruses, influenza viruses, respiratory syncytial viruses, hepatitis viruses and retroviruses (such as HTLV-I, HTLV-II, HIV1 and HIV2). Protozoan parasites and fungi (including yeasts and molds) are also detectable. Other detectable species would be readily apparent to one skilled in the art. The invention is particularly useful for the detection of the presence of nucleic acid associated with various bacteria or viruses.

In a preferred embodiment, the invention is useful for the isolation, amplification and detection of nucleic acids associated with HIV1, HIV2, proviral HIV1, proviral HIV2, cytomegalovirus, human papilloma virus, mycobacterial species, hepatitis virus or genetic diseases.

Prior to contact with the weakly basic polymer defined herein, nucleic acids can be extracted from the specimen in any suitable manner. Various lysing procedures are known in the art, including those described by Laure et al in The Lancet, pp. 538–540 (Sep. 3, 1988), Maniatis et al, *Molecular Cloning: A Laboratory Manual*, pp. 280–281 (1982), Gross-Belland et al in Eur. J. Biochem., 36, 32 (1973) and U.S. Pat. No. 4,965,188 (noted above). Extraction of DNA from whole blood or components thereof is described, for example, in EP-A-0 393 744 (published Oct. 24, 1990), U.S. Pat. No. 5,231,015 (Cummins et al) and U.S. Pat. No. 5,334,499 (Burdick et al), the noted patents being incorporated herein by reference. The lysing procedure may be dependent upon the type of specimen being used as the source of nucleic acids.

While the particular lysing procedure is not critical to the practice of this invention, a preferred lysing procedure includes heating the specimen in the presence of a suitable nonionic surfactant, a number of which are well known in the art. Another useful lysing procedure is described in U.S. Ser. No. 08/063,169 (filed May 18, 1993 by Ekeze and Kerschner) whereby a whole blood specimen is mixed with a buffered solution of ammonium chloride, followed by additional steps which includes a second mixing with ammonium chloride.

The lysate is then mixed, at a pH less than 7 (preferably less than 5), with a weakly basic polymer (defined below) in an amount sufficient to complex with all nucleic acids present in the lysate, forming a water-insoluble precipitate. This polymer is water-soluble at acidic pH. Generally, the amount of polymer present is at least about 0.01 weight percent, with from about 0.05 to about 0.5 weight percent preferred. Of course, a skilled artisan would know how to adjust the amount of polymer to accommodate any quantity of nucleic acids. Mixing can be carried out in any suitable manner for up to 30 minutes (generally less than 5 minutes) and at any suitable temperature (generally from 15° to 35° C.).

The weakly basic polymer can be used in its water-soluble free form, or attached to a water-insoluble substrate, such as in an affinity column, or attached to polymeric, glass or other inorganic particles. Thus, the polymers can be attached using conventional means (for example, absorption, covalent bonds or specific binding reactions) to a suitable substrate, including glass, polymeric or magnetic particles, filters or films. Where the weakly basic polymer is water-insoluble even at basic pH, it can be removed through filtration, centrifugation or other conventional means after the nucleic acids are released.

While bound to the weakly basic polymer, however, the nucleic acids are not useful. It is then necessary to separate the water-insoluble precipitate from the remainder of the sample which may contain considerable cellular debris and excess polymer. This separation can be achieved using any of various conventional procedures, including centrifugation or filtration after which the liquid is discarded. Centrifugation is preferred in the practice of this invention.

After the separation step, the nucleic acids can be decomplexed or released from the weakly basic polymer, by contacting the precipitate with a base, with or without heating. Strong bases may be used without heating, and they include, but are not limited to, sodium hydroxide, potassium hydroxide, ammonium hydroxide, lithium hydroxide, sodium carbonate, sodium bicarbonate, a tertiary amine (such as triethylamine, diisopropylethylamine and lutidine), tricine, bicine or any other organic or inorganic base which would be readily apparent to one skilled in the art. Useful weaker bases may include basic buffers such as tris(hydroxymethyl)aminomethane (or acid addition salts thereof), N,N-bis(2-hydroxyethyl)glycine, N-tris(hydroxymethyl)methyl-glycine, and others well known in the art. Heating may be necessary when weaker bases are used.

Such heating can be carried out for up to 15 minutes (generally less than 5 minutes) at a temperature that is at least about 50° C., and preferably is from about 95° to about 125° C., under suitable pressure. As used in this paragraph, "about" refers to ±5° C.

In preferred embodiments, weaker bases can be used with heating, to release the nucleic acids from the precipitate. This provides a solution containing nucleic acids which are ready for amplification without further treatment. Such weaker bases may be buffers, such as tris(hydroxymethyl)aminomethane hydrochloride.

In some embodiments, the polymers used in such embodiments are those (defined below) which are water-insoluble even at basic pH. Such polymers can be removed from the system after release of nucleic acids and prior to amplification if desired.

The resulting solution containing released nucleic acids has a basic pH. In some instances, the nucleic acids can be further treated without any further adjustment in pH. In other embodiments where a strong base is used, the pH of the solution may be adjusted (generally downward) to from about 6 to about 9 (preferably from about 7.5 to about 9), using any suitable acid or buffer, such as tris(hydroxymethyl)aminomethane hydrochloride, N,N-bis(2-hydroxyethyl)glycine, N-tris(hydroxymethyl)methylglycine and others which would be readily apparent to one skilled in the art. The amounts of such materials needed to achieve the desired pH would be readily apparent to one skilled in the art.

At basic pH, the polymer used for capture of nucleic acids can be either water-soluble or water-insoluble, and monomers needed for providing such properties are described below.

The described method of capturing and releasing nucleic acids of this invention is typically carried out within about 20 minutes, and preferably within about 10 minutes.

As used herein, unless otherwise noted, the modifier "about" refers to a variance of 110% of the noted values. When used with pH values, "about" refers to ±0.5 pH unit.

In a preferred embodiment of this invention, a method for the amplification and detection of a target nucleic acid comprises:

I) lysing cells or virus particles to release a target nucleic acid,

II) subjecting the target nucleic acid to the steps of:
   A) at a pH of less than 7, contacting the target nucleic acid with a water-soluble, weakly basic polymer in an amount sufficient to form a water-insoluble precipitate of the weakly basic polymer with all nucleic acids present in the lysate, including the target nucleic acid,
   B) separating the water-insoluble precipitate from the lysate, and
   C) contacting the precipitate with a base to raise the solution pH to greater than 7, and thereby releasing the nucleic acids, including the target nucleic acid, from the weakly basic polymer, the weakly basic polymer comprising recurring units derived by addition polymerization of one or more ethylenically unsaturated polymerizable monomers having an amine group which can be protonated at acidic pH, III) without further adjustment of pH, amplifying the released target nucleic acid, and IV) detecting the amplified target nucleic acid.

In the foregoing method, it is still more preferred that the weakly basic polymer is water-insoluble at basic pH, and the method further comprises the step of removing the water-insoluble polymer after release of the target nucleic acid but prior to amplification thereof.

The weakly basic polymer used in the practice of this invention is prepared from one or more ethylenically unsaturated polymerizable monomers, at least one of which has an amine group which can be protonated at acidic pH. Thus, at acidic pH, the polymer is protonated to form the acid addition salt of the amine. At basic pH, the polymer exists as the free base.

Particular "weakly basic groups" which can be a part of polymerizable monomers useful in this invention include, but are not limited to, cyclic amine groups, or primary, secondary or tertiary aminoalkyl groups which can be protonated at acidic pH. Useful cyclic amine groups include, but are not limited to, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl groups. The preferred groups are cyclic groups which are aromatic, and the imidazolyl group is most preferred. Useful aminoalkyl or cyclic amine groups are linked to vinyl groups of the monomers using convenient linking groups including alkylene, amido or ester groups, and multiple alkylene groups can be linked together with imino, oxy, amide, carbonyl or ester groups.

Generally useful polymers for capturing nucleic acids are comprised of recurring units derived by addition polymerization of:

a) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl, b) from 0 to about 35 weight percent of a nonionic, hydrophilic ethylenically unsaturated polymerizable monomer, and C) from 0 to about 85 weight percent of a nonionic, hydrophobic ethylenically unsaturated polymerizable monomer.

Preferably, the weakly basic polymer is comprised of recurring units of from about 20 to about 100 weight percent of a), from 0 to about 25 weight percent of b), and from 0 to about 80 weight percent of c).

A more specific class of monomers useful in a) above are those represented by the structure (I):

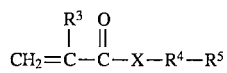

wherein $R^3$ is hydrogen or methyl, and X is oxy or imino. In addition, $R^4$ is a divalent hydrocarbon linking group having from 1 to 8 carbon and hetero atoms in the chain and comprising one or more alkylene groups (such as methylene, ethylene, n-propylene, isopropylene and n-pentylene), providing that when there is more than one alkylene group, they are linked together in $R^4$ with one or more carbonyl, oxy, imino, ester or amido groups in any operable combination. By "operable combination" is meant that those groups can be combined with the alkylene groups in any chemically possible configuration, and can be used in combination (connected to each other) in chemically possible ways (such as oxycarbonyl, carbonamido and others readily apparent to one skilled in the art). It is also to be understood that $R^4$ can be terminated (or connected to $R^5$) with a carbonyl, oxy, imino, ester or amido group.

$R^5$ is a cyclic amine or primary, secondary or tertiary aminoalkyl group, as defined above, which can be protonated at acidic pH.

Examples of useful type a) monomers include, but are not limited to, 1-vinylimidazole, 2-methyl-1-vinylimidazole, 2-vinylpyridine, 1-hydroxy-6-vinyl-1H-benzotriazole, 2-aminoethyl methacrylate hydrochloride, 2-aminoethyl acrylate hydrochloride, N-(3aminopropyl)methacrylamide, 2-vinylquinoline, N-(3imidazolylpropyl)methacrylamide, N-(2-imidazolylethyl)methacrylamide, N-(3-imidazolylpropyl)acrylamide, N-(1,1-dimethyl-3-N-imidazolylpropyl)acrylamide, N-(imidazolylmethyl)acrylamide, 1-vinylpyrrolidinone, 3-(N,N-dimethylamino)propyl metharcylate and acid addition salts of the noted free bases.

A class of novel monomers of type a) of this invention can be used to prepare either homopolymers or copolymers. These monomers are defined by the structure (II):

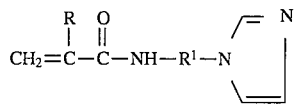

wherein R is hydrogen or methyl. Preferably, R is methyl. In addition, $R^1$ is branched or linear alkylene of 1 to 3 carbon atoms (such as methylene, ethylene, trimethylene or propylene). Preferably, $R^1$ is alkylene of 2 or 3 carbon atoms. More preferably, $R^1$ is trimethylene.

Particularly useful monomers having structure (II) include, but are not limited to, N-(3-imidazolylpropyl)methacrylamide, N-(2-imidazolylethyl)methacrylamide, N-(3-imidazolylpropyl)acrylamide, N-(1,1-dimethyl-3-N-imidazolylpropyl)acrylamide, N-(imidazolylmethyl)acrylamide, and their acid addition salts. Of the novel monomers described herein, the first compound is most preferred.

Preferred type a) monomers include 1-vinylimidazole and N-2-methyl-1-vinylimidazole.

If the monomers of type a) have low or no water solubility, they can also be polymerized in the form of their acid addition salts (such as the hydrochloride or hydrobromide).

Monomers identified as type b) monomers are those which are defined herein as "hydrophilic", meaning those which, when homopolymerized, provide homopolymers which are water-soluble at pH 7 or above. Generally, such monomers have hydrophilic groups such as hydroxy, amine (primary, secondary, tertiary and cyclic), amide, sulfonamide and polyethyleneoxy groups, but it is not necessary that they comprise such groups if the noted homopolymer water-solubility parameter is met.

Representative monomers of type b) include, but are not limited to, acrylamide, 2-hydroxyethyl acrylate, 2,3-dihydroxypropyl acrylate, 2,3-dihydroxypropyl methacrylate, poly(ethyleneoxy)ethyl methacrylate (having 2 to 10 ethyleneoxy groups), and N,N-dimethylacrylamide. A preferred monomer is acrylamide.

Monomers identified as type c) monomers are those which are defined herein as "hydrophobic", meaning those which, when homopolymerized, provide homopolymers which are water-insoluble at pH 7 or above, irrespective of the type of pendant groups they may possess.

Representative monomers of type c) include, but are not limited to, methacrylamide, 2-hydroxyethyl methacrylate, N-t-butylmethacrylamide, ethyl acrylate, methyl acrylate, butyl acrylate, methyl methacrylate, styrene, vinyltoluene and other vinyl aromatics and others which would be readily apparent to one skilled in the art. A preferred monomer is 2-hydroxyethyl methacrylate.

The monomers of types a), b) and c) which are not novel are generally readily available from commercial sources, or prepared using conventional procedures and starting materials.

The novel monomers of structure (II) can be prepared generally by condensation of a 1-(aminoalkyl)imidazole with a (meth)acryloyl chloride using appropriate conditions which would be readily apparent to one skilled in the art. A representative preparation of a preferred monomer is provided below preceeding the examples. More details about such monomers can be obtained from copending and commonly assigned U.S. Ser. No. 08/306,341 filed by Ponticello et al on even date herewith and entitled "Weakly Basic Polymerizable Monomers and Polymers Prepared Therefrom".

The homopolymers and copolymers described herein can be prepared using conventional solution polymerization techniques which are well known in the art, although there are certain preferred conditions which are illustrated in the preparatory methods provided below preceding the Examples. The ratio of various monomers can be adjusted, as one skilled in the art would know, to provide polymers which are either water-soluble or water-insoluble at basic pH, as long as such polymers remain water-soluble at acidic pH.

Solution polymerization generally involves dissolving the monomers in a suitable solvent (including water or various water-miscible organic solvents) and polymerizing in the presence of a suitable free radical initiator. The resulting polymer is water-soluble at acidic pH, so it is precipitated using a solvent such as acetone, purified and redissolved in water for future use.

Particularly useful polymers described herein include, but are not limited to, poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(1-vinylimidazole hydrochloride-co-2-hydroxyethyl methacrylate), poly[N-(1,1-dimethyl-3-imidazolylpropyl)acrylamide]poly(N-2-methyl-1-vinylimidazole) and acid addition salts of the free base polymers.

In preferred embodiments, the polymers used are water-insoluble at basic pH. Such polymers are prepared using type a) monomers as well as type c) monomers but with limited amounts (less than 15 weight of type b) monomers to prevent solubilization of the polymer at basic pH. Representative polymers of this type include, but are not limited to, poly[N-(3-imidazolylpropyl)-methacrylamide hydrochloride-co-2-hydroxyethyl methacrylate], poly(1-vinylimidazole), poly(2-aminoethyl methacrylate hydrochloride-co-2-hydroxyethyl methacrylate) and poly(1-vinylimidazole hydrochloride-co-2-hydroxyethyl methacrylate).

The present invention is also directed to the amplification or detection of one or more specific nucleic acid sequences present in one or more target nucleic acids released as noted above. Moreover, a plurality of target nucleic acids can be amplified and detected simultaneously by using a corresponding set of primers and detection means for each specific nucleic acid. Multiple sequences in the same nucleic acid can also be amplified and detected.

A "PCR reagent" refers to any of the reagents generally considered useful in PCR, namely a set of primers for each target nucleic acid, a DNA polymerase, a DNA polymerase cofactor and two or more deoxyribonucleoside-5'-triphosphates (dNTP's).

As used herein in referring to primers or probes, the term "oligonucleotide" refers to a molecule comprised of four or more deoxyribonucleotides or ribonucleotides, and preferably more than ten. Its exact size is not critical but depends upon many factors including the ultimate use or function of the oligonucleotide. The oligonucleotide may be derived by any method known in the art.

The term "primer" refers to an oligonucleotide, whether naturally occurring or synthetically produced, which is capable of acting as a point of initiation of synthesis when placed under conditions in which synthesis of a primer extension product complementary to a nucleic acid strand (that is, template) is induced. Such conditions include the presence of nucleotides (such as the four standard deoxyribonucleoside-5'-triphosphates), a DNA polymerase and a DNA polymerase cofactor, and suitable temperature and pH. Normally, such conditions are what are known in the art as "high stringency" conditions so that nonspecific amplification is minimized. The primer must be long enough to initiate the synthesis of extension products in the presence of the DNA polymerase. The exact size of each primer will vary depending upon the use contemplated, the complexity of the targeted sequence, reaction temperature and the source of the primer. Generally, the primers used in this invention will have from 10 to 60 nucleotides.

Primers useful herein can be obtained from a number of sources or prepared using known techniques and equipment, including for example, an ABI DNA Synthesizer (available from Applied Biosystems) or a Biosearch 8600 Series or 8800 Series Synthesizer (available from Milligen-Biosearch, Inc.) and known methods for their use (for example as described in U.S. Pat. No. 4,965,188). Naturally occurring primers isolated from biological sources are also useful (such as restriction endonuclease digests). As used herein, the term "primer" also refers to a mixture of primers. Thus, each set of primers for a given target nucleic acid may include two or more primers for each opposing target strand.

One or both primers can be labeled with the same or different label for detection or capture of amplified product. Procedures for attaching labels and preparing primers are well known in the art, for example, as described by Agrawal et al, Nucleic Acid Res., 14, pp. 6227–45 (1986), U.S. Pat. No. 4,914,210 (Levenson et al) relating to biotin labels, U.S. Pat. No. 4,962,029 (Levenson et al) relating to enzyme labels, and the references noted therein. Useful labels also include radioisotopes, electron-dense reagents, chromogens, fluorogens, phosphorescent moieties, ferritin and other magnetic particles (see U.S. Pat. No. 4,795,698 of Owen et al and U.S. Pat. No. 4,920,061 of Poynton et al), chemiluminescent moieties (such as luminol), and other specific binding species (avidin, streptavidin, biotin, sugars or lectins). Preferred labels are enzymes, radioisotopes and specific binding species (such as biotin). Useful enzymes include, glucose oxidase, peroxidases, uricase, alkaline phosphatase and others known in the art and can be attached to oligonucleotides using known procedures. Reagents to provide a colorimetric or chemiluminescent signal with such enzymes are well known.

Where the label is an enzyme such as a peroxidase, at some point in the assay, hydrogen peroxide and suitable dye-forming compositions are added to provide a detectable dye. For example, useful dye-providing reagents include tetramethylbenzidine and derivatives thereof, and leuco dyes, such as water-insoluble triarylimidazole leuco dyes (as described in U.S. Pat. No. 4,089,747 of Bruschi), or other compounds which react to provide a dye in the presence of peroxidase and hydrogen peroxide. Particularly useful dye-providing compositions are described in EP-A-0 308 236 (published Mar. 22, 1989). Chemiluminescent signals in response to a peroxidase label can also be generated using the appropriate reagents.

If one or both primers are biotinylated, the amplified nucleic acid can be detected using detectably labeled avidin or an equivalent thereof (such as streptavidin). For example, avidin can be conjugated with an enzyme, or have a radioisotope using known technology. Biotin on the amplified product complexes with the avidin, and appropriate detection techniques to detect a radioactive, colorimetric or chemiluminescent signal are used.

As used herein, a capture "probe" is an oligonucleotide which is substantially complementary to a nucleic acid sequence of one or more strands of the target nucleic acid, and which is used to insolubilize the amplified nucleic acid. The probe oligonucleotide is generally attached to a suitable water-insoluble substrate such as polymeric or glass beads, microtiter plate well, thin polymeric or cellulosic film or other materials readily apparent to one skilled in the art. The oligonucleotide is generally from about 12 to about 40 nucleotides in length, although the length is not critical.

A DNA polymerase is an enzyme which will add deoxynucleoside monophosphate molecules to the 3+-hydroxy end of the primer in a complex of primer and template, but this addition is in a template dependent manner (that is, dependent upon the specific nucleotides in the template). Many useful DNA polymerases are known in the art. Preferably, the polymerase is "thermostable", meaning that it is stable to heat, especially the high temperatures used for denaturation of DNA strands. More particularly, the thermostable DNA polymerases are not substantially inactivated by the high temperatures used in PCR as described herein.

A number of thermostable DNA polymerases have been reported in the art, including those mentioned in detail in U.S. Pat. No. 4,965,188 (noted above) and U.S. Pat. No. 4,889,818 (Gelfand et al), incorporated herein by reference. Particularly useful polymerases are those obtained from various Thermus bacterial species, such as *Thermus aquaticus, Thermus thermophilus, Thermus filiformis* or *Thermus flavus*. Other useful thermostable polymerases are obtained from a variety of other microbial sources including *Thermococcus literalis, Pyrococcus furiosus,* Thermotoga sp. and those described in WO-A-89/06691 (published Jul. 27, 1989). Some useful polymerases are commercially available. A number of techniques are known for isolating naturally-occurring polymerases from organisms, and for producing genetically engineered enzymes using recombinant techniques, as noted in the art cited in this paragraph.

A DNA polymerase cofactor refers to a nonprotein compound on which the enzyme depends for activity. A number of such materials are known cofactors including manganese and magnesium salts. Useful cofactors include, but are not limited to, manganese and magnesium chlorides, sulfates, acetates and fatty acid salts (for example, butyric, caproic, caprylic, capric and lauric acid salts). The smaller salts, that is chlorides, sulfates and acetates, are preferred.

Also needed for PCR are two or more deoxyribonucleotide-5'-triphosphates, such as dATP, dCTP, dGTP, dUTP or dTTP. Usually, dATP, dCTP, dGTP and dTTP are all used in PCR. Analogues such as dITP and 7-deaza-dGTP are also useful.

Also useful in the practice of the invention is an antibody specific to the DNA polymerase, which antibody inhibits its enzymatic activity at temperatures below about 50° C., but which antibody is deactivated at higher temperatures. Representative monoclonal antibodies having these properties are described in U.S. Pat. No. 5,338,671 (filed Oct. 7, 1992 by Scalice et al), incorporated herein by reference. Antibody fragments can be used in place of the whole molecule if they have equivalent properties.

The PCR reagents described herein are provided and used in PCR in suitable concentrations to provide amplification of the target nucleic acid. The minimal amounts of DNA polymerase is generally at least about 1 unit/100 µl of solution, with from about 4 to about 25 units/100 µl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.075 µmolar with from about 0.2 to about 1 µmolar being preferred. All primers are present in about the same amount (within a variation of 10% of each). The cofactor is generally present in an amount of from about 1 to about 15 mmolar, and each dNTP is generally present at from about 0.1 to about 3.5 mmolar in the reaction mixture. As used in this paragraph, the modifier "about" refers to a variance of ±10% of the noted value.

The PCR reagents can be supplied individually, or in a buffered solution having a pH in the range of from about 7 to about 9 using any suitable buffer.

Since the target nucleic acid to be amplified and detected is usually in double strand form, the two strands must be separated (that is, denatured) before priming can take place. This can occur during the extraction process, but preferably, it occurs in a separate step afterwards. Heating to a suitable temperature (identified as "first temperature" or $T_1$ herein) is a preferred means for denaturation. Generally, this first temperature is in the range of from about 85° to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The denatured strands are then primed with the appropriate sets of primers by cooling the reaction mixture to a second temperature, $T_2$, which is generally within the range of from about 55° to about 70° C. It is desired that cooling is done as quickly as possible, but with presently known equipment, it generally takes place over a time period of from about 5 to about 40 seconds, and more preferably for from about 5 to about 20 seconds.

Once the denatured strands are cooled, the reaction mixture containing the PCR reagents is incubated at a third temperature, $T_3$, generally for from 1 to about 120 seconds, and preferably for from 1 to about 80 seconds, to effect formation of primer extension products. Generally, the third temperature is within the range of from about 55° to about 74° C. Preferably, it is within the range of from about 62° to about 70° C.

In a most preferred embodiment, the second and third temperatures are the same and are within the range of from about 62° to about 70° C. Thus, priming and primer extension are preferably carried out in the same step.

Thus, an amplification cycle comprises the denaturation, priming (or annealing) and primer extension steps described above. Generally, at least 15 of such amplification cycles are carried out in the practice of this invention with the maximum number of cycles being within the discretion of the particular user. In most instances, 15 to 50 amplification cycles are used in the method with 15 to 40 cycles being preferred. Each amplification cycle is generally from about 20 to about 360 seconds, with a cycle time of from about 30 to about 120 seconds being preferred and from about 30 to about 90 seconds being more preferred. However, longer or shorter cycle times can be used if desired.

When used in reference to time for a given step in the amplification procedure, the term "about" refers to ±10% of that time limit. Moreover, when used in reference to temperatures, the term "about" refers to ±5° C.

The amplification method of this invention is preferably conducted in a continuous, automated manner so that the reaction mixture is temperature cycled in a controlled manner for a desired number of times. A number of instruments have been developed for this purpose, as one of ordinary skill in the art would know. Preferably, the instrument used will also be programmable for both primary and secondary amplification cycles.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (Devaney, Jr. et al), incorporated herein by reference. Also described therein are means for heating and cooling the test pack at repeated intervals (that is, through cycles) appropriate for the method of the present invention. Further details regarding useful PCR processing equipment can be obtained from the considerable literature in the field, and would be readily known by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and U.S. Pat. No. 5,229,297 (Schnipelsky et al), all incorporated herein by reference, and any other suitable container which is readily apparent to one skilled in the art. Such test packs are also known as self-contained test devices which have separate compartments for various reagents used in the method of this invention. The compartments are appropriately connected so reagents and assay solutions can be brought into contact with the capture reagent at appropriate times without opening the device.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products.

In the heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions). One such technique is described in EP-A-0 439 222 (published Sep. 18, 1991). Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10 μmeters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. The capture probe can be affixed, for example, to a flat support in the self-contained test device of this invention. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The present invention can also be used in what are known as "homogeneous" amplification procedures in which target nucleic acids are detected without the need for capture reagents. The details of such assays are known in the art, such as in EP-A-0 487 218 (published May 27, 1992) and EP-A-0 512 334 (published Nov. 11, 1992).

The amplification reaction composition can be included as one individually packaged component of a test kit useful for various amplification assays. The kit can include other reagents, solutions, equipment and instructions useful in the method of this invention, including capture reagents immobilized on a water-insoluble substrate, wash solutions, lysing solutions, detection reagents and other materials readily apparent to one skilled in the art. In addition, the test kit can include a separately packaged weakly basic polymer as described above, buffers, weak or strong bases and other reagents needed for either or both amplification and specimen sample preparation. The test kit can also include a test device containing one or more other kit components. This test device is preferably "self-contained" as that term is understood in the art. Other kits can include the weakly basic polymer described herein and one or more reagents (such as detection or capture probes) used in hybridization assays.

The following examples are included to illustrate the practice of this invention, and are not meant to be limiting in any way. All percentages are by weight unless otherwise noted.

MATERIALS AND METHODS FOR EXAMPLES

Preparation of N-(3-Imidazolylpropyl)-methacrylamide

This procedure shows the preparation of a novel monomer of structure (I), identified above, but the preparation is representative of how other monomers within the scope of this invention could readily be prepared.

A solvent mixture was prepared by mixing water (100 ml) containing sodium hydroxide (12.8 g, 0.32 mole) and dichloromethane (200 ml) containing 1-(3-aminopropyl)imidazole (37.5 g, 0.3 mole), and cooled in an ice bath. To this cooled mixture was added all at once, methacryloyl chloride (34.8 g, 0.3 mole) in dichloromethane (100 ml) with vigorous stirring under a nitrogen atmosphere. Heat was evolved with the temperature of the mixture rising to about 60° C., and the mixture was vigorously stirred for another 10 minutes, and then the organic layer was allowed to separate. The water layer was extracted twice with dichloromethane (100 ml each time). The combined organic solution (the organic solvent layer and extracts) was washed with saturated sodium chloride (100 ml), dried over anhydrous sodium sulfate, filtered, and the solvent was removed. The residue was dissolved in chloroform (50 ml), followed by the addition of ethyl ether (50 ml) to the cloud point.

The resulting reaction product crystallized at about 0° C., and was filtered to give a white solid having a melting point of 45°–46° C. The yield was 70%.

Analytical data included: m/e (M-193),

1H NMR (DMSO d6) 1.8 (m,2H,C—$CH_2$—C,$CH_3$), 3.02 (m,2H,N—$CH_2$), 3.95 (t,2H, im-$CH_2$), 5.25 and 5.6 (AB, 2H,vinyl-$CH_2$), 6.82 and 7.15 (AB,2H,4,5-H of im), 7.6 (s,1H,2-H of im), 7.95 (m, 1 H,NH).

Preparation of Homopolymer

A preferred homopolymer prepared from a novel monomer described herein was prepared by adding 2,2'-azobis(2-methylpropionitrile) (300 mg) to a solution of N-(3-imidazolylpropyl)methacrylamide (12.5 g, 0.065 mole) in water (90 ml) and isopropanol (10 ml), maintained under a nitrogen atmosphere. The resulting solution was heated, while being stirred, to 65°–70° C. in a water bath for 3 hours. After about 1.5 hours of that time, concentrated HCl (3 ml) was added, and the stirring was continued under nitrogen for the remaining time. The solution was then concentrated on a rotary evaporator to about 25 ml, and the resulting polymer product was precipitated in acetone (over 4 liters), filtered and dissolved in deionized water (80 ml). The solution contained 12% solids.

Preparation of First Copolymer

Poly[N-(3-imidazolylpropyl)methacrylamide hydrochloride-co-acrylamide] (90:10 weight ratio) was prepared by adding 2,2'-azobis(2-methylpropionitrile) (400 mg) to a solution of N-(3-imidazolylpropyl)methacrylamide (18 g, 0.09 mole) and acrylamide (2 g, 0.028 mole) in deionized water (120 ml) and isopropanol (15 ml), maintained under a nitrogen atmosphere. The solution was heated to 65°–70° C. with stirring for 4 hours, followed by addition of dilute HCl to lower the pH to about 2. Stirring and heating were continued for another hour, and the solution was then allowed to reach room temperature overnight.

The solution was concentrated to about 75 ml using a rotary evaporator, and the resulting polymer was precipitated in acetone (about 4 liters), filtered and dissolved in deionized water (150 ml). Further concentration to about 125 ml was carried out to remove residual acetone. The polymer was present at 15.5% solids.

Preparation of Second Copolymer

Poly[2-aminoethyl methacrylate hydrochloride-co-2-hydroxyethyl methacrylate] (20:80 weight ratio) was prepared by adding 2,2'-azobis(2-methylpropionitrile) (400 mg) to a solution of 2-aminoethyl methacrylate hydrochloride (4 g, 0.02 mole) and 2-hydroxyethyl methacrylate (16 g, 0.12 mole) in deionized water (180 ml) and ethanol (20 ml), maintained under a nitrogen atmosphere. The solution was heated to 65°–70° C. with stirring for 4 hours. Stirring and heating were continued for another hour, and the solution was then allowed to reach room temperature overnight.

The resulting polymer was precipitated in acetone (about 4 liters), filtered and dissolved in deionized water (150 ml). Further concentration to about 125 ml was carried out to remove residual acetone. The polymer was present at 5.6% solids.

Preparation of Third Copolymer

Poly[1-vinylimidazole-co-2-hydroxyethyl methacrylate] (50:50 weight ratio) was prepared by adding 2,2'-azobis(2-methylpropionitrile) (350 mg) to a solution of 1-vinylimidazole (10 g, 0.1 mole) and 2-hydroxyethyl methacrylate (10 g, 0.077 mole) in N,N-dimethylformamide (160 ml), maintained under a nitrogen atmosphere. The solution was heated to 65°–70° C. with stirring for 7 hours.

After sitting at room temperature overnight, the polymer was precipitated in acetone (about 4 liters), filtered and dissolved in deionized water (200 ml) containing concentrated HCl (8.5 ml). Further concentration was carried out to remove residual acetone. The polymer was present at 12.4% solids.

Preparation of Fourth Copolymer

Poly(1-vinylimidazole-co-2-hydroxyethyl methacrylate) (25:75 weight ratio) was prepared in a fashion like the "Third Copolymer". The resulting solution contained 13.7% solids.

Recombinant DNA polymerase from *Thermus aquaticus* was prepared using conventional methods, and had an activity of about 250,000 units/mg of protein.

The following primers and probes were prepared using known starting materials and procedures using an Applied Biosystems Model 380B DNA synthesizer and standard phosphoramidite chemistry and the ABI 1 μmolar scale, fast cycle protocol. Nucleoside-3'-phosphoramidites and nucleoside derivatized controlled pore glass supports were obtained from Applied Biosystems.

Primers and probes complementary to the major capsid protein region of human cytomegaloviral DNA were as follows:

SEQ ID:NO:1

5'-X-CATTCCCACT GACTTTCTGA CGCACGT-3'

SEQ ID:NO:2

5'-X-TGAGGTCGTG GAACTTGATG GCGT-3'

SEQ ID:NO:3

5'-GGTCATCGCC GTAGTAGATG CGTAAGGCCT-Y-3'.

Primers and probes complementary to the 65 kD antigen region of *Mycobacterium tuberculosis* DNA were as follows:

SEQ ID:NO:4

5'-X-GAGATCGAGC TGGAGGATCC GTACG-3'

SEQ ID:NO:5

5'-X-AGCTGCAGCC CAAAGGTGTT GGACT-3'

SEQ ID:NO:6

5'-CGAAATCGCT GCGGTGGCCG CAATCTGCTC-Y-3'.

Primers and probes complementary to the gag region of HIV1 proviral DNA were as follows:

SEQ ID:NO:7

5'-X-TTTGGTCCTT GTCTTATGTC CAGAATGC-3'

SEQ ID:NO:8

5'-X-ATAATCCACC TATCCCAGTA GGAGAAAT-3'

SEQ ID:NO:9

5'-ATCCTGGAAT TAAATAAAAT AGTAAGAATG TATAGCCCTA C-Y-3'.

In the primer sequences, X represents a biotin phosphoramidite moiety (from DuPont) attached to the sequence through two tetraethylene glycol spacer units using the teaching of U.S. Pat. No. 4,914,210 (Levenson et al), incorporated herein by reference. All purifications were carried out using a nucleic acid purification column, followed by reversed phase HPLC techniques.

The capture probe sequences, Y contains two tetraethylene glycol spacers connected by a phosphate linkage, and a 3-amino-1,2-propanediol moiety prepared using the procedures of the Levenson et al patent noted above.

Low copy HIV1 target proviral DNA was extracted from the 8E5/LAV cell line (contains a single integrated copy of the HIV-I genome) using conventional procedures. Following cell lysis and protein digestion, the nucleic acid was purified by phenol/chloroform extraction: tris-saturated phenol (750 μl) was added to the cell suspension, and phenol/lysate solutions were mixed and separated by centrifugation. The aqueous phase was then transferred into a fresh 2 ml tube. This procedure was repeated using chloroform isoamyl alcohol. The aqueous layer was brought to 0.3 molar with sodium acetate. Nucleic acids were precipitated by adding 95% cold ethanol, and stored at −70° C. for 1 hour. The concentration of HIV1 proviral DNA was then determined at $A_{260}$ and serial dilutions of varying copy number were made in "TE" buffer [tris(hydroxymethyl)aminomethane (1 mmolar) and (ethylenedinitrilo)tetraacetic acid (0.1 mmolar)] for use in the experiments. Sample (5–10 μl) was added to the DNA solution for capture.

Control hCMV strain AD169 (ATCC VR538) was propagated in MRC-5 (ATCC CCL171) cells until characteristic cytopathic effect was evident in >90% of the monolayer. Cell culture fluid was harvested, 20% final volume fetal bovine serum was added, and the cells were pelleted. The supernatant containing free virus was frozen at −80° C. For control DNA amplifications, 1:10 serial dilutions of this stock preparation were made into buffer solution [tris(hydroxymethyl)aminomethane (10 mmolar, pH 8) and TWEEN™ 20 nonionic surfactant (0.5%)]. The serial dilutions were then boiled for 5 minutes to lyse the viral particles and aliquots of these samples were added to the PCR reaction mixture.

*Mycobacterium tuberculosis* DNA was obtained by diluting cultured *M. tuberculosis,* an avirulent strain H37Ra (ATCC 25177), to the same turbidity as a MacFarland #1 standard. This corresponds to approximately $3 \times 10^8$ colony-forming units/ml (cfu). For DNA amplifications, 1:10 serial dilutions of this stock preparation were made into buffer solution identified above. The serial dilutions were then boiled for 30 minutes to lyse the bacteria. A level of target nucleic acid corresponding to $1.8 \times 10^4$ cfu was used in each 300 μl reaction mixture.

Clinical samples for Example 3 were obtained from Dr. Gregory J. Buffone at Baylor College of Medicine, Texas Children's Hospital (Houston, Tex.). These samples had been previously determined to be either hCMV DNA "culture positive" or "culture negative". Culture positive samples were further scored by the length of time required for culture positive results to be visually observed (samples which are visually positive at earlier times are generally assumed to contain more culturable virus).

Deoxyribonucleotides (dNTP's), tris(hydroxymethyl)aminomethane buffer and lyophilized calf thumus DNA were obtained from Sigma Chemical Co.

ZONYL™ FSP anionic fluorinated phosphate ester surfactant was obtained from DuPont.

TWEEN™ 20 nonionic surfactant was obtained from ICI Americas, Inc.

The monoclonal antibody specific to the noted DNA polymerase was prepared as described in U.S. Pat. No. 5,338,671 (noted above).

A streptavidin-peroxidase conjugate solution comprised a commercially available (Zymed Laboratories, Inc.) conjugate of streptavidin and horseradish peroxidase (131 ng/ml), casein (0.5%), 4'-hydroxyacetanilide (10 mmolar) and merthiolate (0.5%) in phosphate buffered saline solution (25 mmolar sodium phosphate and 75 mmolar sodium chloride). The final conjugate concentration was 312 ng/ml.

A wash solution (pH 7.4) contained sodium phosphate, monobasic 1-hydrate (25 mmolar), sodium chloride (373 mmolar), (ethylenedinitrilo)tetraacetic acid disodium salt (2.5 mmolar), ethylmercurithiosalicylic acid sodium salt (25 μmolar), and decyl sodium sulfate (38 mmolar).

The dye-providing composition (pH 6.8) contained 4,5-bis(4-dimethylaminophenyl)-2-(4-hydroxy-3-methoxyphenyl)imidazole leuco dye (250 μmolar), poly(vinyl pyrrolidone) (112 mmolar), hydrogen peroxide (0.03%), diethylenetriaminepentaacetic acid (100 μmolar), 3'-chloro-4'-hydroxyacetanilide (5 mmolar) and sodium phosphate, monobasic, 1-hydrate (10 mmolar).

The aqueous dye signal stop solution contained sodium azide (0.1%).

The capture reagents were prepared by attaching SEQ ID NO:3, SEQ ID NO:6 or SEQ ID NO:9 oligonucleotide identified above to particles of poly[styrene-co-3-(p-vinylbenzylthio)propionic acid] (95:5 weight ratio, 1 μm average diameter) in the following manner. A suspension of the particles in water was washed twice with 2-(N-morpholino)ethanesulfonic acid buffer (0.1 molar, pH 6), and suspended to approximately 10% solids. A sample (3.3 ml) of the washed particles, diluted to 3.33% solids in the buffer (0.1 molar), was mixed with 1-(3-dimethylaminopropyl)-3-ethylcarbodiimide hydrochloride (2.1 ml of 84 mg/ml water) and the appropriate probe (22 μl of 44.44 OD/ml nanopure water). The resulting suspension was heated at 50° C. in a water bath for about two hours with intermittent mixing and centrifuged. The particles were washed three times with tris(hydroxymethyl)aminomethane buffer (0.01 molar, pH 8) containing (ethylenedinitrilo)tetraacetic acid disodium salt (0.001 molar) and resuspended therein to 4% solids.

A PCR reaction mixture (100 ml) included tris(hydroxymethyl)aminomethane hydrochloride buffer (10 mmolar, pH 8), potassium chloride (50 mmolar), magnesium chloride (10 mmolar), gelatin (0.01%), dATP, dCTP, dGTP and dTTP (1.5 mmolar of each in Examples 2 and 3 and 1.0 mmolar of each in Example 4), glycerol (9.5%), primers (0.4 μmolar of each unless otherwise indicated), DNA polymerase identified above (16 units/100 μl), and a monoclonal antibody specific to DNA polymerase identified above (50:1 molar ratio to DNA polymerase, in Examples 2 and 4 only).

Amplification by PCR was carried out in Example 2 below using disposable chemical test packs or devices which contained chambers for individual reagents and solution. These chambers and device were formed from a sheet of polyester (0.01 cm thickness) coated with polyethylene (SCOTCH PAK™ from 3M Co.), folded over to provide a circular chamber about 1.3 cm in diameter. An opening was provided to permit the addition of the PCR reagent mixture which was drawn into a chamber by vacuum. The opening was then heat sealed. After amplification, a corner of the chamber was cut, and the reaction mixture containing products, was transferred to a microfuge tube (0.5 ml) for storage at 4° C. until detection of the products was carried out. The PCR protocol was carried out using a conventional automated PCR processor which is described in detail in U.S. Pat. No. 5,089,233, incorporated herein by reference.

Amplification in Examples 3 and 4 were carried out in 0.2 ml MICROAMP™ reaction tubes using a conventional Perkin Elmer GENEAMP™ PCR System 9600 thermocycler.

The PCR amplification protocols are described below in the respective examples.

SURECELL™ test devices were used to detect amplification products. These devices are available from Eastman Kodak Company (Clinical Diagnostics Division), and contain three test wells, each with a mounted LOPRODYNE™ microporous membrane (Pall Corp., 5 μmeter average pore size). Upon dilution to 0.25%, each capture reagent (1.2 μl) was disposed and dried in defined regions of the membranes in the test wells of the test devices. These test devices are described in more detail in U.S. Pat. No. 4,948,561 (Hinckley et al), incorporated herein by reference.

Detection was carried out in the following manner. A portion (5 μl) of the final amplification reaction mixture was mixed with a buffer solution [tris(hydroxymethyl)aminomethane (10 mmolar, pH 8), potassium chloride (50 mmolar), magnesium chloride (10 mmolar) and gelatin (0.01%] (95 μl) and incubated at 95° C. for 5 minutes to denature the nucleic acids. The resulting solution was then transferred to SURECELL™ test devices so that amplified target nucleic acids could be hybridized to the capture probes at 50° C.

The test wells of the test devices were then washed at 55° C. with a buffer solution [sodium dihydrogen phosphate (10 mmolar), sodium chloride (150 mmolar), sodium decyl sulfate (1%) and ethylenediaminetetraacetic acid (1 mmolar)] (250 μl pH 7.4). The streptavidin-peroxidase conjugate solution (50 μl) was added to each test well, and allowed to flow through the membranes at room temperature. After two minutes, the test wells were washed a second time.

The dye-providing composition (100 μl) was then applied to each test well, followed by incubation at room temperature for two minutes. The dye stop solution (100 μl) was then added to each test well to stop dye development, and the resulting dye signal was visually graded on a density scale of 0 to 10 (highest density). Background readings were obtained from the regions on the membranes where no capture reagent had been deposited.

Gel electrophoresis was carried out by adding the amplification product mixture (6.75 μl) to agarose gels (2.5%) which had been prestained with ethidium bromide (0.4 mg/ml final concentration). The gels were electrophoresed at about 8 volts/cm for about 1 hour using an electrophoresis buffer (600 ml) containing ethidium bromide (0.4 mg/ml final concentration). The buffer was a mixture of tris(hydroxymethyl)aminomethane, borate and ethylenediaminetetraacetic acid. The resulting bands were compared to conventional molecular weight markers, and the product band intensity was scored (115-mer for HIV1 and 383-mer for *M. tuberculosis*) on a 0 to 5 scale with 0 representing no detectable signal and 5 representing the highest signal.

Other reagents and materials were obtained either from commercial sources or prepared using readily available starting materials and conventional procedures.

EXAMPLE 1 CAPTURE AND RELEASE OF DNA USING WEAKLY BASIC HOMOPOLYMER

This example illustrates the practice of the present invention to capture and release a nucleic acid using poly(1-vinylimidazole).

Various volumes of poly(1-vinylimidazole) [of a 1:10 dilution of 2.4% stock solution (pH 2.3)] were mixed with calf thymus DNA (100 μl, 0.5 μg/μl) and vortexed to form a precipitate of nucleic acid and polymer. Centrifuging for 1 minute was then carried out. An additional amount of polymer (10 μl of the 2.4% stock solution) was added to each supernatant and the resulting mixtures were vortexed and centrifuged to determine if the first precipitation was quantitative. Table I below shows the amount of polymer used and the type of precipitation observed for each sample.

TABLE I

| Polymer Volume (μl) | First Precipitation Pellet | Second Precipitation Pellet |
|---|---|---|
| 5 | Barely Visible | Large |
| 10 | Small to medium | Small |
| 25 | Large | Not visible |
| 50 | Very large | Not visible |

It was observed that precipitation occurred under acidic conditions (pH 2.3), and that 50 μl of the 1:10 dilution of polymer stock solution could be used to precipitate 100 μl of the calf thymus DNA solution (0.5 μg/μl) in a nearly quantitative fashion. This observation was also confirmed using conventional gel electrophoretic methods.

Experiments were conducted to determine how to solubilize the precipitate, thereby releasing the nucleic acid for later use. Table II below shows the various pellet solubilization conditions attempted and the resulting pellet size. The most useful technique was the use of heat in combination with basic pH (no pellet). Conventional gel electrophoresis clearly indicated that at basic pH, the polymer and nucleic acids were present as free materials. Thus, the nucleic acids were available for later use, such as in PCR.

TABLE II

| Solubilizing Conditions | Pellet Size |
|---|---|
| 50 μl NaCl (4 molar) | None |
| 50 μl NaOH (50 mmolar) with heating at 55° C. for 5 minutes | Small |
| 50 μl NaOH (100 mmolar) with heating at 55° C. for 5 minutes | None |
| 50 μl NaOH (50 mmolar) with heating at 100° C. for 10 minutes | None |
| 50 μl NaOH (25 mmolar) with heating at 100° C. for 10 minutes | None |
| 50 μl "TE" buffer* with heating at 100° C. for 10 minutes | Large |
| 50 μl water with heating at 100° C. for 10 minutes | Large |
| 50 μl Zonyl ™ FSP nonionic surfactant (1.25%) with heating at 100° C. for 10 minutes | Large |
| 50 μl "TW" buffer** with heating at 100° C. for 10 minutes | Large |

*"TE" buffer includes ethylenediaminetetraacetic acid (1 mmolar) in tris(hydroxymethyl))aminomethane hydrochloride buffer (10 mmolar, pH 8).
**"TW" buffer includes TWEEN ™ 20 nonionic surfactant (0.5%) in tris(hydroxymethyl)aminomethane hydrochloride buffer (10 mmolar, pH 8).

Table III below shows the affect of pH on the formation of a precipitate between the polymer (50 μl of 1:10 dilution of stock solution) and calf thymus DNA (100 μl of 0.5 μg/μl solution). Acidic pH was clearly required for effective capture of the nucleic acid by formation of a precipitate (pellet).

TABLE III

| pH | Pellet Size |
|---|---|
| 2.3 | Large |
| 3 | Large |
| 4 | Large |
| 7 | Clear, thick mass |
| 12 | Barely visible |

EXAMPLE 2 CAPTURE AND RELEASE OF HIV1 PROVIRAL DNA AND AMPLIFICATION OF HIV1 AND GENOMIC MYCOBACTERIUM TUBERCULOSIS DNA

This example demonstrates the practice of this invention to capture and release a target nucleic acid in the presence of non-target nucleic acids, followed by amplification of the isolated target nucleic acids.

Samples for the experiments were prepared by mixing calf thymus DNA (non-target DNA, 250 μl, 0.5 μg/μl), with or without 100 copies of HIV1 proviral DNA, with poly(1-vinylimidazole) (125 μl of 1:10 dilution of 2.4% solution), vortexing to form precipitates, and centrifuging for 1 minute to isolate the precipitates.

The precipitates were resuspended in either a solution sodium hydroxide (187.5 μl, 50 mmolar) in water (25 μl), or aqueous sodium hydroxide and ZONYL™ FSP anionic fluorinated phosphate ester surfactant (25 μl), followed by heating at 100° C. for 10 minutes. Tris(hydroxymethyl)aminomethane hydrochloride buffer (37.5 μl, 0.5 molar) was then added to each solution bringing the final DNA concentration to 0.5 μg/μl. The anionic surfactant was added to some precipitates to determine its effect on the release and amplification of DNA.

To each resulting mixture (60 or 150 μl) was added the PCR amplification reaction mixture (240 or 150 μl) identified above to give a final reaction mixture of 300 μl, and amplification was carried out for 40 cycles using the following protocol:

1) denaturation at 95° C. for 15 seconds (80 seconds for first cycle), and 2) primer annealing and primer extension for 30 seconds at 62° C. for target HIV1 provital DNA.

*M. tuberculosis* DNA (100 copies) was similarly amplified (primer extension at 64° C. in step 2), except that it was added directly to the PCR reaction mixture. It was not subjected to the weakly basic polymer. This was to demonstrate that the polymer would not adversely affect amplification of a non-captured target nucleic acid.

After amplification, two methods were used to detect the presence of amplified target DNA:

(a) Gel electrophoresis: An aliquot (12 μl) of each amplified product solution was added to 4 μl of a conventional sample tracking dye. The resulting mixture was loaded onto a 2.5% agarose gel that was prestained with ethidium bromide (0.4 mg/ml final concentration). Electrophoresis was carried out for 1.5 hours at 120 volts. Gel bands were visualized under ultraviolet light and scored as described above.

(b) Dye signal in SURECELL™ test devices were obtained as described above.

Table IV below shows the gel electrophoresis and dye color score results for several samples under various conditions. The results show that HIV1 proviral DNA target nucleic acid was successfully amplified after capture and released using the weakly basic polymer. In addition, the *M. tuberculosis* DNA was also amplified, indicating that the polymer in the reaction mixture did not inhibit amplification of an exogenously added nucleic acid.

Dye signals and gel electrophoresis results at the 30 μg and 75 μg target levels were consistent with those obtained with the same quantities of boiled or unboiled calf thymus DNA (samples 17–20), or unboiled human placental DNA (samples 21–23). At all levels of ZONYL™ FSP anionic surfactant, amplification was severely inhibited, and no signal was observed with either detection technique. Samples 1 and 2 demonstrated the most efficient amplification for HIV1 provital DNA (24 and 60 copies per 300 μl reaction mixture, respectively).

TABLE IV

| Sample | Volume (ml) | Final % Zonylä FSP | Amplified Target DNA | Dye Signal Score | Gel Signal |
|---|---|---|---|---|---|
| 1 | 60 | 0 | HIV1 | 9.0 | 1.5 |
| 2 | 150 | 0 | HIV1 | 9.5 | 2.5 |
| 3 | 60 | 0.5 | HIV1 | 0 | 0 |
| 4 | 150 | 0.5 | HIV1 | 0 | 0 |
| 5 | 60 | 0.25 | HIV1 | 0 | 0 |
| 6 | 150 | 0.25 | HIV1 | 0 | 0 |
| 7 | 60 | 0.0125 | HIV1 | 0 | 0 |
| 8 | 150 | 0.0125 | HIV1 | 0 | 0 |
| 9 | 60 | 0 | Mtb* | 8.5 | 2.5 |
| 10 | 150 | 0 | Mtb* | 8.5 | 1.5 |
| 11 | 60 | 0.5 | Mtb* | 0 | 0 |
| 12 | 150 | 0.5 | Mtb* | 0 | 0 |
| 13 | 60 | 0.25 | Mtb* | 0 | 0 |
| 14 | 150 | 0.25 | Mtb* | 0 | 0 |
| 15 | 60 | 0.0125 | Mtb* | 0 | 0 |
| 16 | 150 | 0.0125 | Mtb* | 0 | 0 |
| 17 | 60 ml unboiled calf thymus DNA | 0 | Mtb* | 8.5 | 2.5 |
| 18 | 150 ml unboiled calf thymus DNA | 0 | Mtb* | 8.0 | 2.0 |
| 19 | 60 ml boiled calf thymus DNA | 0 | Mtb* | 8.5 | 2.5 |
| 20 | 150 ml boiled calf thymus DNA | 0 | Mtb* | 8.5 | 2.0 |
| 21 | 19.8 ml human placental DNA | 0 | Mtb* | 8.5 | 2.5 |
| 22 | 60 ml human placental DNA | 0 | Mtb* | 8.5 | 2.0 |
| 23 | 150 ml human placental DNA | 0 | Mtb* | 8.5 | 2.0 |

*"Mtb" = *Mycobacterium tuberculosis*

EXAMPLE 3 SAMPLE PREPARATION AND AMPLIFICATION OF HUMAN CYTOMEGALOVIRAL DNA

This example demonstrates the practice of the present invention using 9 hCMV "culture positive" and 3 "culture negative" urine specimens obtained from a medical center. It also compares the present invention with a commonly used sample preparatory method, that is, heating the sample to 100° C. for 10 minutes in the presence of a nonionic surfactant.

Two aliquots (150 μl each) of each urine specimen were mixed with a buffer solution (150 μl) containing TWEEN™ 20 nonionic surfactant (0.5%) and calf thymus DNA (10 μg) in tris(hydroxymethyl)aminomethane hydrochloride buffer (10 molar, pH 8).

The mixtures were each heated at 100° C. for 10 minutes. To one set of specimens, a weakly basic polymer, poly(1-vinylimidazole) (125 μl, 1:10 dilution of 2.4%), was added, forming a precipitate of polymer and nucleic acids. The resulting suspensions were centrifuged at 14,000 rpm for 5 minutes. The supernatants were discarded, and the pellets were resuspended in sodium hydroxide (83 μl, 50 mmolar) and heated at 100° C. for 10 minutes to release the nucleic acids. Tris(hydroxymethyl)aminomethane hydrochloride (17 μl, 0.5 molar, pH 7) was then added to neutralize the solution.

The second set of specimens received no further treatment.

An aliquot (20 μl) of each solution (for both sets of treated specimens) was added to the PCR reagent mixture (80 μl) described above containing the noted hCMV primers, and 40 cycles of PCR were carried out using the following protocol:

1) denaturation at 94° C. for 30 seconds, and 2) primer annealing and primer extension for 30 seconds at 64° C.

Detection of amplified products was achieved using dye color signal generation with capture probes as described above in Example 2 and compared to the results determined by culture (clinical specimens only).

FIG. 1 and Table V below show the results of both methods, compared with culture results. It is apparent that, in this example, this invention demonstrated a sensitivity of 89% (8 out of 9 culture positive specimens), and a specificity of 100% (3 out of 3 culture negative specimens) when compared with culture results. The control sample preparatory method (heating in the presence of a nonionic surfactant) displayed a sensitivity of 33% (3 out of 9 culture positive specimens) and a specificity of 100% (3 out of 3 culture negative specimens) when compared with the culture results.

This example demonstrates the advantage of removing target nucleic acids from inhibitors which may be present in clinical specimens. Other methods used in the art can accomplish the same result, but in a more tedious, time-consuming and environmentally unsafe manner.

TABLE V

| Specimen | Culture Result (Days) | Dye Signal Score Invention | Dye Signal Score Control |
|---|---|---|---|
| U5 | +14 | 5 | 0 |
| U6 | — | 0 | 0 |
| U15 | — | 0 | 0 |
| U17 | — | 0 | 0 |
| U19 | +10 | 8 | 6 |
| U29 | +7 | 5 | 0 |
| U44 | +17 | 6 | 0 |
| U60 | +7 | 7 | 0 |
| U67 | +7 | 6 | 3 |
| U73 | +4 | 8 | 6 |
| U90 | +10 | 7 | 0 |
| U100 | +14 | 0 | 0 |
| Control-1:10,000 dilution | Not available | 7 | 0 |
| Control-1:10$^5$ dilution | Not available | 5 | 0 |
| Control-1:10$^6$ dilution | Not available | 2 | 0 |
| Negative Control (water only) | Not available | 0 | 0 |

EXAMPLE 4 CAPTURE AND RELEASE OF TARGET hCMV DNA AND AMPLIFICATION USING SEVERAL POLYMERS

This example was carried out similarly to Example 3 above using several weakly basic polymers within the scope of this invention.

Various hCMV DNA dilutions (10 μl) were mixed, by vortexing, with a buffer solution (70 μl) containing tris(hydroxymethyl)aminomethane hydrochloride buffer (10 molar, pH 8) and TWEEN™ 20 nonionic surfactant (0.5%), and with calf thymus DNA (20 μl, 0.5 μg/μl) in 1.5 ml microcentrifuge tubes. Diluted polymer (100 μl, about 0.24% solids) was added to each tube, and the resulting mixture vortexed.

Polymer 1 was poly[N-(3-imidazolylpropyl)-methacrylamide hydrochloride] (12% solids), Polymer 2 was poly[N-vinylimidazole-co-2-hydroxyethyl methacrylate] (50:50 weight ratio, 5.3 % solids), and Polymer 3 was poly[N-(3-imidazolylpropyl)methacrylamide hydrochloride-co-acrylamide] (90:10 weight percent, 15.5% solids). Negative Controls were similarly prepared and processed containing no target nucleic acid. Other controls contained target nucleic acids, but distilled water (100 μl) was mixed with the specimens instead of polymer.

The resulting mixtures were centrifuged at 14,000 rpm for 30 seconds to separate any precipitate from the supernatant which was discarded. To the resulting pellets were added the buffer (100 μl, identified above containing TWEEN™ 20 nonionic surfactant, pH 10), followed by vortexing and heating at 100° C. for 5 minutes.

The dilution levels of target hCMV DNA stock solutions were as follows:

Level 1: 1:500

Level 2: 1:5,000

Level 3: 1:50,000

Level 4: 1:500,000

Amplification and detection of the captured and released target hCMV DNA was carried out similarly to that described in Example 3, using 40 cycles of the protocol:

1) denaturation at 95° C. for 30 seconds (180 seconds for first cycle), and 2) primer annealing and primer extension for 30 seconds at 68° C.

The results are shown in FIG. 2 and in Table VI below. In FIG. 2, the first three sets of bars show the dye color scores obtained by the invention from the hCMV DNA levels captured and subsequently amplified for each of three weakly basic polymers. The last set of bars show the results when no polymer was used to isolate nucleic acids. The dye scores in Table VI were determined as described in Example 3 above.

The results indicate that the three weakly basic polymers effectively captured and released target nucleic acid for amplification except at the lowest target nucleic acid level.

TABLE VI

| Sample | Polymer | Dilution Level | Dye Signal Score |
|---|---|---|---|
| 1 | 1 | 1 | 8 |
| 2 | 1 | 2 | 6 |
| 3 | 1 | 3 | 3 |
| 4 | 1 | 4 | 0 |
| 5 | 1 | * | 0 |
| 6 | 2 | 1 | 8 |
| 7 | 2 | 2 | 6 |
| 8 | 2 | 3 | 4 |
| 9 | 2 | 4 | 0 |
| 10 | 2 | * | 0 |
| 11 | 3 | 1 | 8 |
| 12 | 3 | 2 | 5 |
| 13 | 3 | 3 | 3 |
| 14 | 3 | 4 | 0 |
| 15 | 3 | * | 0 |
| 16 | None | 1 | 0 |
| 17 | None | 2 | 0 |
| 18 | None | 3 | 0 |

TABLE VI-continued

| Sample | Polymer | Dilution Level | Dye Signal Score |
|---|---|---|---|
| 19 | None | 4 | 0 |
| 20 | None | * | 0 |

*Control = no target DNA

The invention has been described in detail with particular reference to preferred embodiments thereof, but it will be understood that variations and modifications can be effected within the spirit and scope of the invention.

We claim:

1. A method for providing a nucleic acid from a lysate comprising the steps of:
   A) at a pH of less than 7, contacting a lysate suspected of containing a nucleic acid with a water-soluble, weakly basic polymer comprised of recurring units derived by addition polymerization of:
      1) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pryidazinyl, pyrimidyl, pyrazinyl, quinolinyl and quinazolinyl,
      2) from 0 to about 35 weight percent of a nonionic, hydrophilic ethylenically unsaturated polymerizable monomer, and
      3) from 0 to about 85 weight percent of a nonionic, hydrophobic ethylenically unsaturated polymerizable monomer in an amount sufficient to form a water-insoluble precipitate of said weakly basic polymer with all nucleic acids present in said lysate,
   B) separating said water-insoluble precipitate from said lysate, and
   C) contacting said precipitate with a base to raise the solution pH to greater than 7, and thereby releasing said nucleic acids from said weakly basic polymer,
   said weakly basic polymer comprising recurring units derived by addition polymerization of one or more ethylenically unsaturated polymerizable monomers having an amine group which can be protonated at acidic pH.

2. The method of claim 1 further comprising the step:
   D) adjusting the pH of said solution containing said released nucleic acids to from about 6 to about 9.

3. The method of claim 1 wherein said base is sodium hydroxide, potassium hydroxide, ammonium hydroxide, lithium hydroxide, sodium carbonate, sodium bicarbonate, a tertiary amine or tris(hydroxymethyl)-aminomethane.

4. The method of claim 1 wherein said weakly basic polymer is used in step A) in an amount of from about 0.01 to about 0.5 weight %.

5. The method of claim 1 wherein a weak base is used in step C), accompanied by heating said water-insoluble precipitate at from about 50° to about 125° C.

6. The method of claim 1 wherein a strong base is used in step C) without heating said water-insoluble precipitate.

7. A method for the amplification and detection of a target nucleic acid comprising:
   I) providing a target nucleic acid using the steps of:
   A) at a pH of less than 7, contacting a lysate suspected of containing a target nucleic acid with a water-soluble, weakly basic polymer comprised of recurring units derived by addition polymerization of:
      1) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl,
      2) from 0 to about 35 weight percent of a nonionic, hydrophilic ethylenically unsaturated polymerizable monomer, and
      3) from 0 to about 85 weight percent of a nonionic, hydrophobic ethylenically unsaturated polymerizable monomer in an amount sufficient to form a water-insoluble precipitate of said weakly basic polymer with all nucleic acids present in said lysate, including said target nucleic acid,
   B) separating said water-insoluble precipitate from said lysate, and
   C) contacting said precipitate with a base to raise the solution pH to greater than 7, and thereby releasing said nucleic acids, including said target nucleic acid, from said weakly basic polymer,
   said weakly basic polymer comprising recurring units derived by addition polymerization of one or more ethylenically unsaturated polymerizable monomers having an amine group which can be protonated at acidic pH,
   II) amplifying said target nucleic acid present among said released nucleic acids, and
   III) detecting said amplified target nucleic acid.

8. The method of claim 7 further comprising, after step C), the step:
   D) adjusting the pH of the solution containing said released nucleic acids to from about 6 to about 9.

9. The method of claim 7 wherein said amplifying is accomplished by polymerase chain reaction using a thermostable DNA polymerase and at least one labeled primer.

10. The method of claim 7 for the amplification and detection of a target nucleic acid associated with HIV1, HIV2, proviral HIV1, proviral HIV2, cytomegalovirus, Mycobacterium spp., human papilloma virus, hepatitis viruses or a genetic disease using primers specific to and hybridizable with the strands of said target nucleic acid.

11. The method of claim 8 wherein said weakly basic polymer is comprised of recurring units of from about 20 to about 100 weight percent of (a), from 0 to about 25 weight percent of (b), and from 0 to about 80 weight percent of (c).

12. The method of claim 8 wherein monomer (a) has the formula (I):

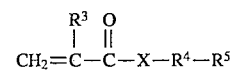

wherein $R^3$ is hydrogen or methyl,

X is oxy or imino, $R^4$ is a divalent hydrocarbon linking group having from 1 to 8 carbon or hetero atoms in the chain and comprising one or more alkylene groups, provided that when there are more than one alkylene group, they are linked together in $R^4$ with one or more carbonyl, oxy, imino, ester or amido groups in any operable combination, and $R^4$ can be terminated with carbonyl, oxy, imino, ester or amido group, and $R^5$ is a cyclic amine or primary, secondary or tertiary aminoalkyl group which can be protonated at acidic pH.

13. The method of claim 12 wherein said monomer (a) has the structure (II):

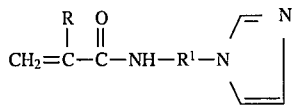

wherein R is hydrogen or methyl, and $R^1$ is alkylene of 1 to 3 carbon atoms.

14. The method of claim 8 wherein:

monomer (a) is selected from the group consisting of N-(3-imidazolylpropyl)methacrylamide, 1-vinylimidazole, 2-methyl-1-vinylimidazole, 2-vinylpyridine, 1-hydroxy-6-vinyl-1H-benzotriazole, 2-aminoethyl methacrylate hydrochloride, 2-aminoethyl acrylate hydrochloride, 1-vinylpyrrolidinone, 3-(N,N-dimethylamino)propyl methacrylate, 2-aminoethyl methacrylate, N-(3-aminopropyl)methacrylamide hydrochloride, 2-vinylquinoline, N-(2-imidazolylethyl)methacrylamide, N-(3-imidazolylpropyl)acrylamide, N-(imidazolylmethyl)acrylamide, N-(1,1-dimethyl-3-imidazolylpropyl)acrylamide and acid addition salts thereof, monomer (b) is selected from the group consisting of acrylamide, 2-hydroxyethyl acrylate, 2,3-dihydroxypropyl acrylate, 2,3-dihydroxypropyl methacrylate, poly(ethyleneoxy)ethyl methacrylate (having 2 to 10 ethyleneoxy groups), and N,N-dimethyl acrylamide, and monomer (c) is selected from the group consisting of methacrylamide, 2-hydroxyethyl methacrylate, N-t-butylmethacrylamide, ethyl acrylate, methyl methacrylate, styrene, vinyltoluene, methyl acrylate and butyl acrylate.

15. The method of claim 8 wherein said weakly basic polymer is poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(1-vinylimidazole-co-2-hydroxyethyl methacrylate), poly[N-(1,1-dimethyl-3-imidazolylpropyl)acrylamide] and poly(N-2-methyl-1-vinylimidazole).

16. A test kit for amplification of a target nucleic acid comprising, separately packaged:

a) an amplification reaction mixture comprising one or more amplification reagents, and b) a weakly basic polymer comprised of recurring units derived by addition polymerization of:

1) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl, 2) from 0 to about 35 weight percent of a nonionic, hydrophilic ethylenically unsaturated polymerizable monomer, and 3) from 0 to about 85 weight percent of a nonionic, hydrophobic ethylenically unsaturated polymerizable monomer.

17. The test kit of claim 16 wherein said amplification reaction mixture comprises a set of primers, at least one of which is labeled, a plurality of dNTP's and a thermostable DNA polymerase.

18. The test kit of claim 16 comprising a test device containing one or more kit components.

19. The test kit of claim 16 wherein said weakly basic polymer is attached to a solid substrate.

20. A method for the amplification and detection of a target nucleic acid comprising:

I) lysing cells or virus particles to release a target nucleic acid,

II) subjecting said target nucleic acid to the steps of:

A) at a pH of less than 7, contacting said target nucleic acid with a water-soluble, weakly basic polymer comprised of recurring units derived by addition polymerization of:

1) from about 15 to 100 weight percent of a water-soluble, weakly basic ethylenically unsaturated polymerizable monomer having at least one group which can be protonated at acidic pH and which is selected from the group consisting of aminoalkyl, imidazolyl, isoxazolyl, pyridyl, piperidyl, piperazinyl, pyrazolyl, triazolyl, tetrazolyl, oxadiazolyl, pyridazinyl, pyrimidyl, pyrazinyl, quinolinyl and quinazolinyl, 2) from 0 to about 35 weight percent of a nonionic, hydrophilic ethylenically unsaturated polymerizable monomer, and 3) from 0 to about 85 weight percent of a nonionic, hydrophobic ethylenically unsaturated polymerizable monomer in an amount sufficient to form a water-insoluble precipitate of said weakly basic polymer with all nucleic acids present in said lysate, including said target nucleic acid, B) separating said water-insoluble precipitate from said lysate, and C) contacting said precipitate with a base to raise the solution pH to greater than 7, and thereby releasing said nucleic acids, including said target nucleic acid, from said weakly basic polymer, said weakly basic polymer comprising recurring units derived by addition polymerization of one or more ethylenically unsaturated polymerizable monomers having an amine group which can be protonated at acidic pH, III) without further adjustment of pH, amplifying said released target nucleic acid, and IV) detecting said amplified target nucleic acid.

21. The method of claim 20 wherein said weakly basic polymer is water-insoluble at basic pH, and said method further comprises the step of removing said water-insoluble polymer after release of said target nucleic acid therefrom and prior to amplification thereof.

* * * * *